US00PP20787P2

(12) United States Plant Patent
Head et al.

(10) Patent No.: US PP20,787 P2
(45) Date of Patent: Feb. 23, 2010

(54) ***TERNSTROEMIA* PLANT NAMED 'HOHB'**

(50) Latin Name: *Ternstroemia gymnanthera*
Varietal Denomination: HOHB

(75) Inventors: William A. Head, Seneca, SC (US); Robert H. Head, Seneca, SC (US); Lisa Jones Head, Seneca, SC (US)

(73) Assignee: Head Ornamentals, Inc., Seneca, SC (US)

( * ) Notice: Subject to any disclaimer, the term of this patent is extended or adjusted under 35 U.S.C. 154(b) by 0 days.

(21) Appl. No.: 12/283,266

(22) Filed: Sep. 8, 2008

(51) Int. Cl.
*A01H 5/00* (2006.01)

(52) U.S. Cl. ..... Plt./226

(58) Field of Classification Search ..... Plt./226
See application file for complete search history.

(56) References Cited

U.S. PATENT DOCUMENTS

PP11,735 P2 * 1/2001 Berry ..... Plt./226

* cited by examiner

*Primary Examiner*—Wendy C. Haas
(74) *Attorney, Agent, or Firm*—C. A. Whealy

(57) ABSTRACT

A new and distinct cultivar of *Ternstroemia* plant named 'HOHB', characterized by its compact, upright and outwardly spreading plant form; uniformly mounded habit; dense and bushy plant habit; vigorous growth habit; leaves that are initially bright yellow in the spring, becoming golden bronze in the summer and green highlighted with yellow in the late autumn and winter; and good garden performance.

3 Drawing Sheets

Botanical designation: *Ternstroemia gymnanthera.*
Cultivar denomination: 'HOHB'.

BACKGROUND OF THE INVENTION

The present Invention relates to a new and distinct cultivar of *Ternstroemia*, botanically known as *Ternstroemia gymnanthera* and hereinafter referred to by the name 'HOHB'.

The new *Ternstroemia* is a product of a planned breeding program conducted by the Inventors in Seneca, S.C. The objective of the breeding program is to create new *Ternstroemia* cultivars with attractive plant form and leaf coloration.

The new *Ternstroemia* originated from a self-pollination made by the Inventors in 1997, in Seneca, S.C. of an unnamed selection of *Ternstroemia gymnanthera*, not patented. The new *Ternstroemia* was discovered and selected by the Inventors as a single plant from within the progeny of the stated self-pollination in a controlled outdoor nursery environment in Seneca, S.C. in 1998.

Asexual reproduction of the new cultivar by semi-hardwood and hardwood stem cuttings in Seneca, S.C. since November, 2000 has shown that the unique features of this new *Ternstroemia* plant are stable and reproduced true to type in successive generations of asexual reproduction.

SUMMARY OF THE INVENTION

Plants of the new *Ternstroemia* have not been observed under all possible environmental conditions. The phenotype may vary somewhat with variations in environment such as temperature and/or light intensity without, however, any variance in genotype. The following traits have been repeatedly observed and are determined to be the unique characteristics of 'HOHB'. These characteristics in combination distinguish 'HOHB' as a new and distinct cultivar of *Ternstroemia:*

1. Compact, upright and outwardly spreading plant form; uniformly mounded habit.

2. Dense and bushy plant habit.
3. Vigorous growth habit.
4. Leaves that are initially bright yellow in the spring, becoming golden bronze in the summer and green highlighted with yellow in the late autumn and winter.
5. Good garden performance.

Plants of the new *Ternstroemia* can be compared to plants of the parent selection. Plants of the new *Ternstroemia* differ from plants of the parent selection in the following characteristics:

1. Plants of the new *Ternstroemia* are more compact than and not as vigorous as plants of the parent selection.
2. Plants of the new *Ternstroemia* are denser than and not as open as plants of the parent selection.
3. During the spring and summer, plants of the new *Ternstroemia* have bright yellow to golden bronze-colored leaves whereas plants of the parent selection have green-colored leaves.

Plants of the new *Ternstroemia* can be compared to the plants of *Ternstroemia gymnanthera* 'Variegata', not patented. In side-by-side comparisons conducted in Seneca, S.C., plants of the new *Ternstroemia* differed from plants of 'Variegata' in the following characteristics:

1. Plants of the new *Ternstroemia* were more compact than and not as upright as plants of 'Variegata'.
2. Plants of the new *Ternstroemia* were denser than and not as open as plants of 'Variegata'.
3. During the spring and summer, plants of the new *Ternstroemia* had bright yellow to golden bronze-colored leaves whereas plants of 'Variegata' had green, gray and cream-colored leaves tinged with pink.

Plants of the new *Ternstroemia* can be compared to the plants of *Ternstroemia gymnanthera* 'Conthery', disclosed in U.S. Plant Pat. No. 11,735. In side-by-side comparisons conducted in Seneca, S.C., plants of the new *Ternstroemia* differed from plants of 'Conthery' in the following characteristics:

1. Plants of the new *Ternstroemia* were more compact than and not as upright as plants of 'Conthery'.
2. Plants of the new *Ternstroemia* were not as vigorous as plants of 'Conthery'.
3. During the spring and summer, plants of the new *Ternstroemia* had bright yellow to golden bronze-colored leaves whereas plants of 'Conthery' had reddish bronze leaves that changed to green in the late summer.

BRIEF DESCRIPTION OF THE PHOTOGRAPHS

The accompanying colored photographs illustrate the overall appearance of the new *Ternstroemia*. These photographs show the colors as true as it is reasonably possible to obtain in colored reproductions of this type. Colors in the photographs may differ slightly from the color values cited in the detailed botanical description, which accurately describe the colors of the new *Ternstroemia*.

The photograph on the first sheet comprises a side perspective view of a typical plant of 'HOHB' grown in an outdoor nursery.

The photograph on the second sheet is a close-up view of typical leaves of 'HOHB'.

The photograph on the third sheet is a close-up view of a typical flower of 'HOHB'.

DETAILED BOTANICAL DESCRIPTION

The aforementioned photographs and following observations and measurements describe plants grown during the summer in Seneca, S.C. in an outdoor nursery and under commercial production conditions. During the production of the plants, day temperatures ranged from 26° C. to 40° C. and night temperatures ranged from 16° C. to 35° C. Plants used for the photographs and description had been growing for seven years. In the following description, color references are made to The Royal Horticultural Society Colour Chart, 2001 Edition, except where general terms of ordinary dictionary significance are used.

Botanical classification: *Ternstroemia gymnanthera* 'HOHB'.

Parentage: Self-pollination of an unnamed selection of *Ternstroemia gymnanthera*, not patented.

Propagation:

*Type*.—By semi-hardwood and hardwood cuttings.

*Time to initiate roots, summer*.—About 30 to 45 days at temperatures of 26° C. to 38° C.

*Time to initiate roots, winter*.—About 60 to 70 days at temperatures of 16° C. to 21° C.

*Time to produce a rooted young plant, summer*.—About 80 to 90 days at temperatures of 26° C. to 38° C.

*Time to produce a rooted young plant, summer*.—About 120 to 150 days at temperatures of 16° C. to 21° C.

*Root description*.—Medium to coarse, moderately fibrous; close to 172D in color.

*Rooting habit*.—Freely branching; dense.

Plant description:

*Plant form and growth habit*.—Perennial evergreen shrub; compact upright and outwardly spreading plant form; uniformly mounded habit; moderately vigorous.

*Branching habit*.—Freely branching habit; dense and bushy growh habit with numerous lateral branches developing per plant.

*Plant height*.—About 1 meters to 1.4 meters.

*Plant diameter, area of spread*.—About 1.2 meters to 1.5 meters.

*Lateral branch description*.—Length: About 2.5 cm to 33 cm. Diameter: About 1.7 mm to 3.5 mm. Internode length: About 2.5 mm to 21.5 mm. Strength: Strong, flexible. Texture: Smooth, glabrous. Color, young stems: Close to N144B. Color, mature stems: Close to 199C.

*Foliage description*.—Arrangement: Alternate, simple. Length: About 3.5 cm to 6.5 cm. Width: About 1.25 cm to 2.1 cm. Shape: Narrowly elliptic. Apex: Retuse. Base: Cuneate. Margin: Entire. Venation pattern: Pinnate. Texture, upper and lower surfaces: Smooth, glabrous; waxy. Color: Developing leaves, upper surface: Initially close to N172B becoming close to 163A. Developing leaves, lower surface: Close to 145C. Fully expanded leaves, upper surface: Close to 12A becoming close to N144C; venation, close to N172B. In the autumn, color becomes closer to 12A to N144B. Leaf color of plants growing in the shade will be closer to 137A. Fully expanded leaves, lower surface: Close to 145C; venation, close to N172D. Petiole: Length: About 3.2 mm to 6.5 mm. Diameter: About 1.1 mm to 2.6 mm. Texture, upper and lower surfaces: Smooth, glabrous; waxy. Color, upper surface: Between 47A and 46A. Color, lower surface: Close to 47A to 47C.

Flower description:

*Flower arrangement and appearance*.—Single inconspicuous cupped flowers; flowers axillary. Freely flowering habit; about one to three flowers per lateral branch.

*Natural flowering season*.—Plants of the new *Ternstroemia* typically flower during May and June in South Carolina.

*Flower longevity*.—Individual flowers last two to three days on the plant; flowers persistent.

*Fragrance*.—Faint.

*Flower diameter*.—About 8 mm to 12 mm.

*Flower depth*.—About 5 mm to 8 mm.

*Flower bud*.—Length: About 4 mm to 5 mm. Diameter: About 4 mm to 5 mm. Shape: Globular. Color: Close to 157D.

*Petals*.—Arrangement: Single whorl of five imbricate petals fused at the base. Length: About 4 mm to 5 mm. Width: About 4 mm to 5 mm. Shape: Obtuse. Apex: Rounded. Margin: Entire. Texture, upper and lower surfaces: Smooth, glabrous; waxy. Color: When opening and fully opened, upper surface: Close to 157D. When opening and fully opened, lower surface: Close to 157D.

*Sepals*.—Arrangement: Five fused in a single whorl. Length: About 2 mm. Width: About 2 mm. Shape: Ovate. Apex: Acute. Margin: Entire. Texture, upper and lower surfaces: Smooth, glabrous; waxy. Color: Immature, upper and lower surfaces: Close to 157D. Mature, upper and lower surfaces: Close to 157D.

*Peduncles*.—Length: About 1.5 mm to 2.5 mm. Diameter: About 0.7 mm to 1.9 mm. Angle: About 45° to 80° from lateral branch axis. Strength: Strong, flexible. Texture: Smooth, glabrous; waxy. Color: Close to 157D.

*Reproductive organs*.—Androecium: Stamen quantity per flower: About 30 to 40. Anther shape: Oblong. Anther length: About 2 mm. Anther color: Close to 4C. Pollen amount: Abundant. Pollen color: Close to 4C. Gynoecium: Pistil length: About 3 mm. Stigma shape: Bi-lobed. Stigma color: Close to 149D. Style length: About 1 mm. Style color: Close to 157D. Ovary color: Close to 157D.

*Fruits*.—Quantity per lateral branch: About nine to twelve. Length: About 1 cm to 1.2 cm. Diameter: About 9 mm to 11 mm. Texture: Smooth, glabrous. Color: Close to 145C; with development, close to 47C.

*Seeds*.—Length: About 0.3 mm. Diameter: About 5 mm to 6 mm. Color: Close to 34C.

Garden performance: Plants of the new *Ternstroemia* have been observed to have good garden performance and to be tolerant to rain, wind and temperatures ranging from about −25° C. to about 40° C.

Disease/pest resistance: Plants have not been observed to be resistant to pathogens and pests common to *Ternstroemia*.

It is claimed:

1. A new and distinct cultivar of *Ternstroemia* plant named 'HOHB' as illustrated and described.

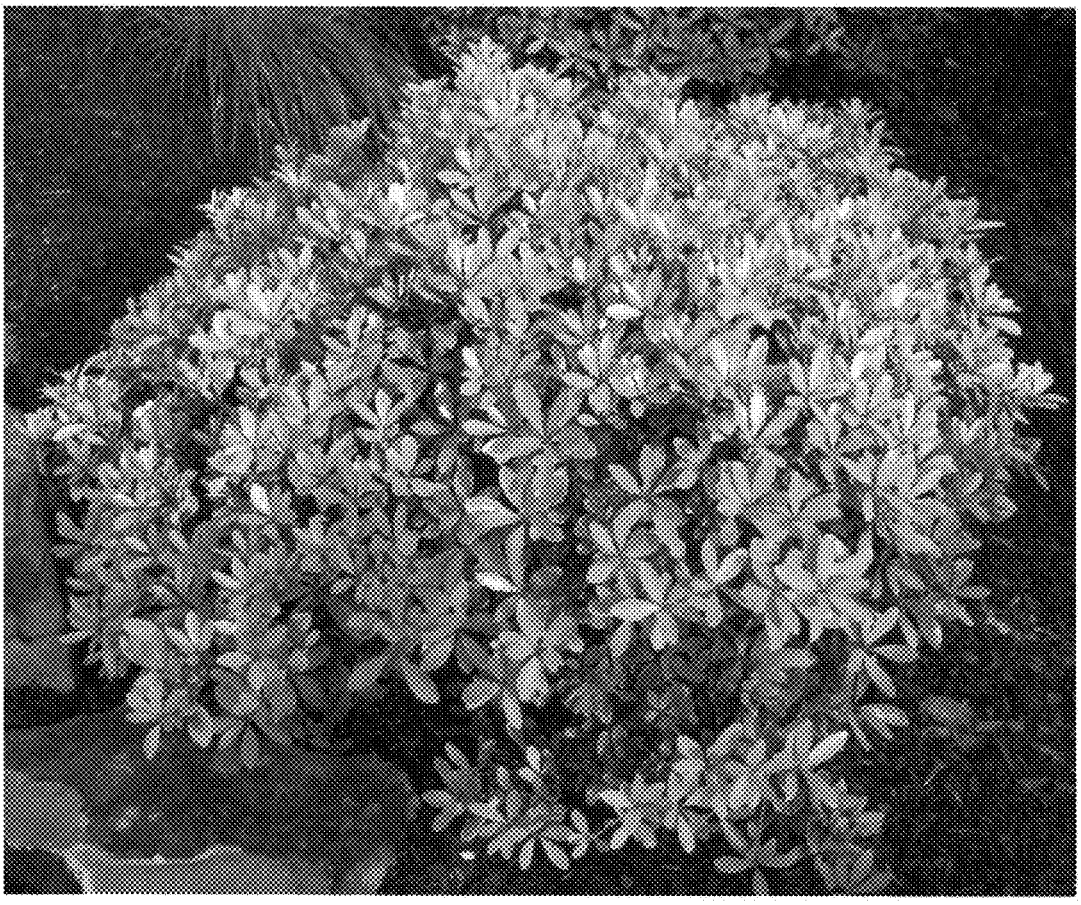

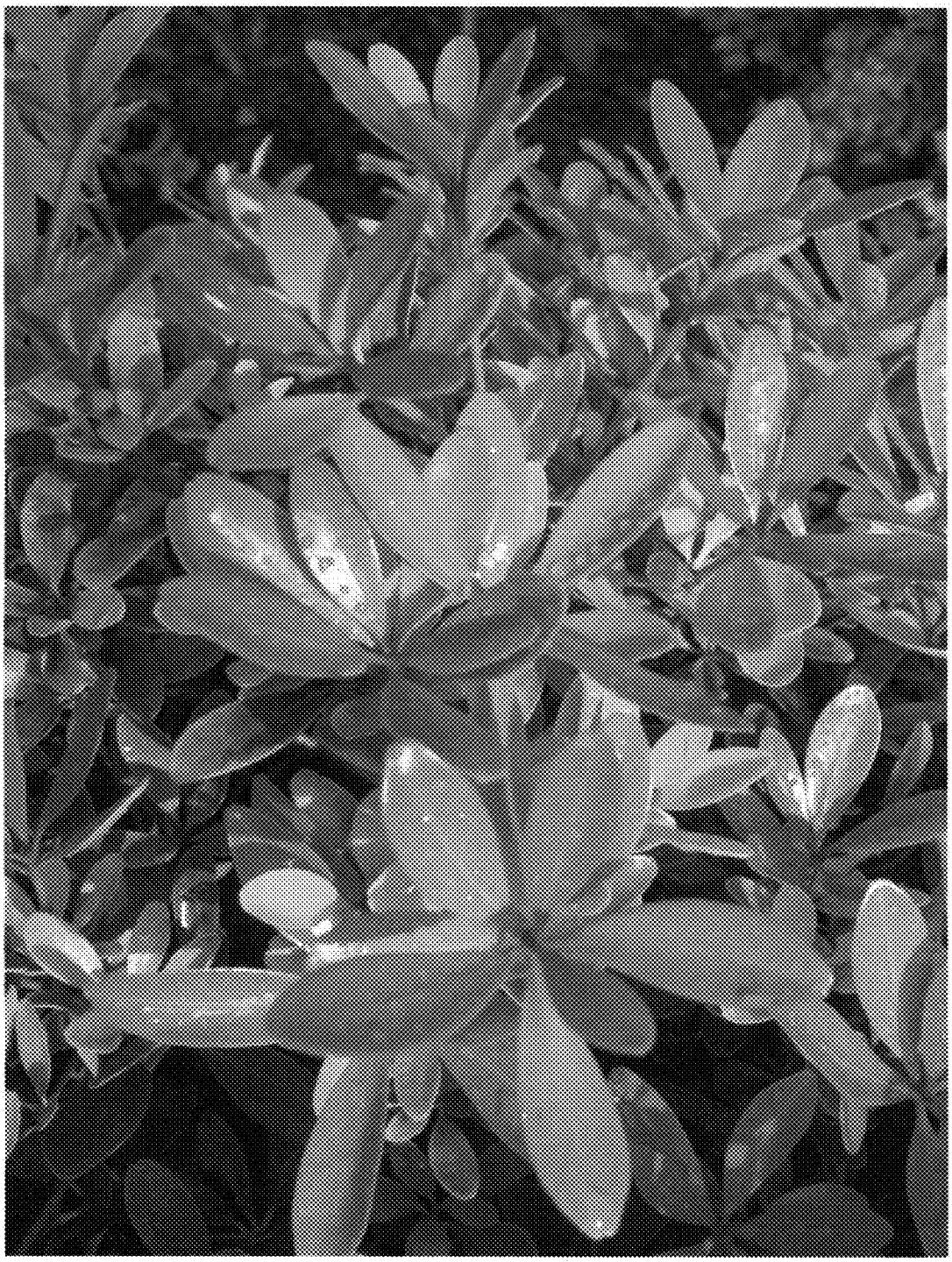

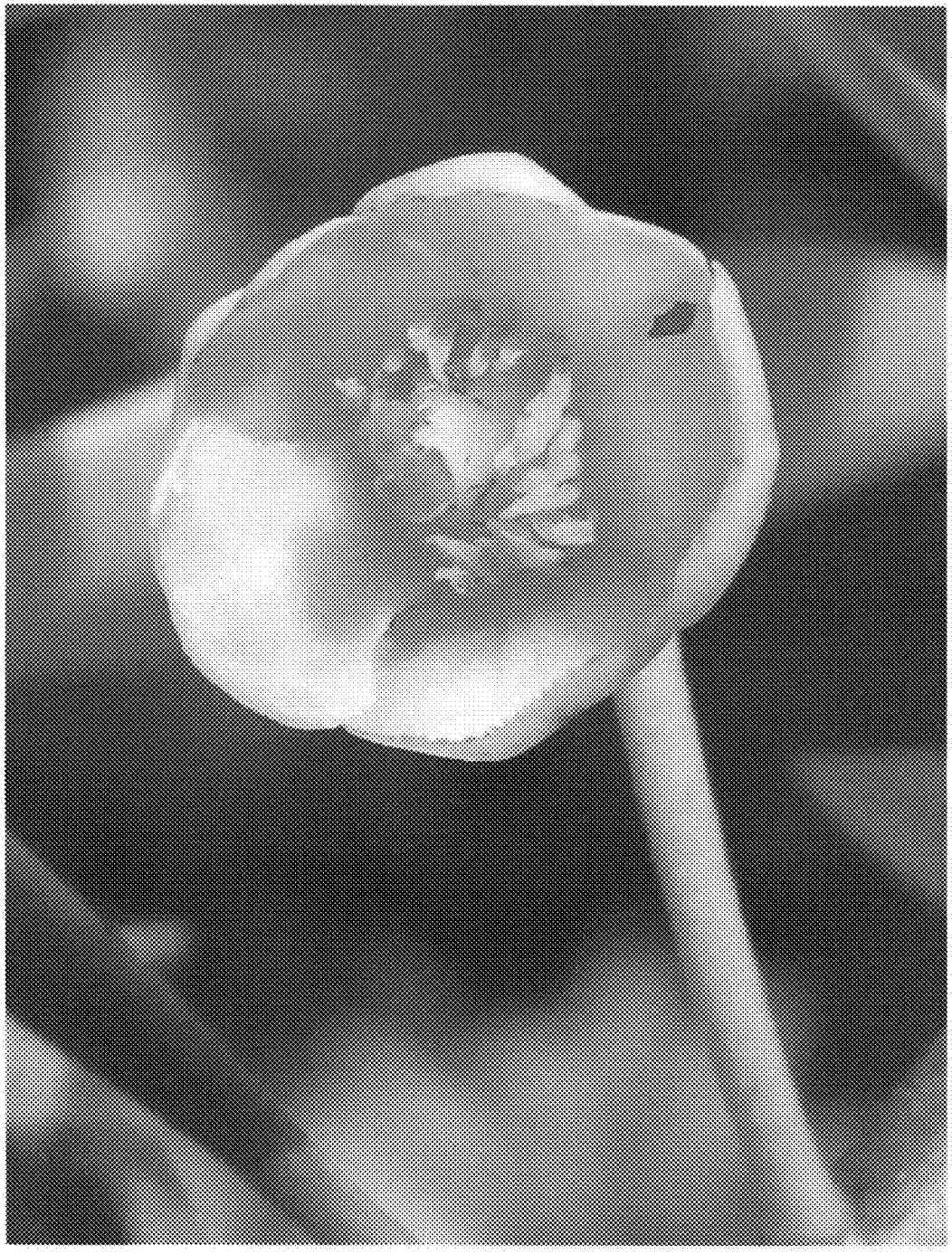

* * * * *